(12) United States Patent
Kajiki et al.

(10) Patent No.: US 10,854,327 B2
(45) Date of Patent: Dec. 1, 2020

(54) DIAGNOSTIC IMAGING SYSTEM

(71) Applicant: Shimadzu Corporation, Kyoto (JP)

(72) Inventors: Shunsuke Kajiki, Kyoto (JP); Daisuke Notohara, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/137,052

(22) Filed: Sep. 20, 2018

(65) Prior Publication Data

US 2019/0103184 A1 Apr. 4, 2019

(30) Foreign Application Priority Data

Oct. 4, 2017 (JP) .................................. 2017-194407

(51) Int. Cl.
*G16H 30/20* (2018.01)
*G16H 10/60* (2018.01)
*G16H 15/00* (2018.01)
*A61B 6/00* (2006.01)
*G16H 40/63* (2018.01)
*G06F 3/0484* (2013.01)

(52) U.S. Cl.
CPC .............. *G16H 30/20* (2018.01); *A61B 6/548* (2013.01); *G16H 10/60* (2018.01); *G16H 15/00* (2018.01); *A61B 6/40* (2013.01); *A61B 6/4283* (2013.01); *G06F 3/0484* (2013.01); *G06T 2210/41* (2013.01); *G16H 40/63* (2018.01)

(58) Field of Classification Search
CPC ........... A61B 6/50; A61B 8/5261; A61B 6/42; A61B 6/548; A61B 6/40; G06F 19/00; G06F 17/3089; G06F 19/321; G06F 19/324; G06F 3/0484; G16H 10/60; G16H 40/20; G16H 15/00; G16H 40/63; G16H 50/70; G16H 30/20; G06T 2210/41
USPC ..................................................... 250/370.09
See application file for complete search history.

(56) References Cited

U.S. PATENT DOCUMENTS

| 4,583,241 A | * | 4/1986 | Walters .................. A61B 6/032 378/19 |
| 2005/0209888 A1 | * | 9/2005 | Oowaki .................. G16H 40/20 705/3 |
| 2008/0312519 A1 | * | 12/2008 | Maschke ................ G16H 40/63 600/345 |
| 2010/0228101 A1 | * | 9/2010 | Maschke .............. A61B 5/0022 600/301 |
| 2010/0303330 A1 | * | 12/2010 | Moriya ................... G16H 30/40 382/132 |
| 2010/0331833 A1 | * | 12/2010 | Maschke ................ G16H 20/40 606/20 |

(Continued)

FOREIGN PATENT DOCUMENTS

| JP | 2010-057684 A | 3/2010 |
| JP | 2014-109835 A | 6/2014 |

OTHER PUBLICATIONS

Kohzoh Makita, "Adrenal Venous Sampling for Primary Aldosteronism—Tips and Tricks for Successful AVS Procedure", Journal of Japan Interventional Radiology Society, 2013, vol. 28, No. 2, p. 204-210.

*Primary Examiner* — Taeho Jo
(74) *Attorney, Agent, or Firm* — Muir Patent Law, PLLC (57) ABSTRACT

This diagnostic imaging system is configured to create report data including a diagnostic image and an analysis result as image data and create sample data including a sampling position and an analysis result as document data.

18 Claims, 5 Drawing Sheets

(56) References Cited

U.S. PATENT DOCUMENTS

| | | | | |
|---|---|---|---|---|
| 2010/0332254 | A1* | 12/2010 | Maschke | A61B 5/411 705/3 |
| 2011/0075901 | A1* | 3/2011 | Nakamura | G16H 30/40 382/128 |
| 2011/0195866 | A1* | 8/2011 | Deppermann | G01N 35/04 506/12 |
| 2012/0290324 | A1* | 11/2012 | Ribbing | G06F 19/321 705/3 |
| 2013/0148779 | A1* | 6/2013 | Notohara | A61B 6/4085 378/22 |
| 2013/0344588 | A1* | 12/2013 | Halushka | C12Q 1/6804 435/309.1 |
| 2015/0269325 | A1* | 9/2015 | Ohta | G06F 3/0482 715/771 |
| 2016/0078596 | A1* | 3/2016 | Ohashi | A61B 6/508 378/62 |
| 2016/0320319 | A1* | 11/2016 | Hench | G01N 23/207 |
| 2018/0075221 | A1* | 3/2018 | Vergaro | G06Q 50/24 |
| 2018/0078231 | A1* | 3/2018 | Butani | A61B 6/5217 |

\* cited by examiner

| Analysis information | | RA1(RA) | RA2(RA) AN(SD) |
|---|---|---|---|
| Sampling position (blood vessel name) | Identification information | Analysis result | Analysis result |
|  |  |  |  |
|  |  |  |  |
|  |  |  |  |
|  |  |  |  |
|  |  |  |  |
|  |  |  |  |

DIAGNOSTIC IMAGING SYSTEM

CROSS-REFERENCE TO RELATED APPLICATIONS

The present application claims priority to Japanese Patent Application No. JP2017-194407, entitled "Diagnostic Imaging System", filed on Oct. 4, 2017, and invented by Shunsuke Kajiki and Daisuke Notohara, the contents of which are hereby incorporated by reference in their entirety.

BACKGROUND OF THE INVENTION

Field of the Invention

The present invention relates to a diagnostic imaging system, and more particularly to a diagnostic imaging system equipped with a radiographic imaging device for capturing a diagnostic image of a subject.

Description of the Background Art

Conventionally, it is known that a diagnosis of diseases caused by tumors and the like in a body/internal organs is performed by sampling a specimen of a subject. Such a diagnosis of diseases is described in "Kohzoh Makita, "Adrenal Venous Sampling for Primary Aldosteronism"—Tips and Tricks for Successful AVS Procedure", Journal of Japan Interventional Radiology Society, 2013, Vol. 28, No. 2, p. 204-210" (hereinafter, "Adrenal Venous Sampling for Primary Aldosteronism").

In the above-described "Adrenal Venous Sapling for Primary Aldosteronism", it is disclosed to perform blood sampling from veins at various areas of adrenal glands for diagnosis of primary aldosteronism by inserting a catheter to a sampling position while confirming the X-ray fluoroscopic image of the subject by the radiographic image diagnostic device in real time.

Then, the blood (specimen) at each position collected by the blood sampling (adrenal vein sampling) from veins at various areas of adrenal glands is analyzed and definitive diagnosis is performed based on the cortisol concentration, etc., as the analysis result.

Further, a diagnostic imaging system equipped with a radiographic imaging device for capturing a diagnostic image of a subject is known. Such a diagnostic imaging system is disclosed in Japanese Unexamined Patent Application Publication No. 2010-57684.

According to the Japanese Unexamined Patent Application Publication No. 2010-57684, when a doctor, etc., prepares a report on the analysis result and the diagnostic image of the subject, the report is created at a report creation terminal device. Here, such a report is generally prepared as images (image data) at a report creation terminal device. Therefore, in a medical department terminal device, since the report is displayed as an image, supplementary information in the report is extracted as information composed of color information and position information (for example, information on the position of each pixel).

In this case, the medical information system described in Japanese Unexamined Patent Application Publication No. 2010-57684 has a disadvantage that it is difficult to extract the supplementary information from the image data of the report as character codes (document data). For this reason, when a doctor, etc., prepares a material by using supplementary information from a report, there is a problem that it takes time and effort to prepare the material.

SUMMARY OF THE INVENTION

The present invention has been made to solve the aforementioned problems, and an object of the present invention is to provide a diagnostic imaging system capable of reducing labor for preparing a document when a doctor, etc., prepares a material from information included in a report.

In order to attain the aforementioned object, a diagnostic imaging system according to one aspect of the present invention includes a radiographic imaging device configured to capture a diagnostic image of a subject from which a specimen is sampled at a sampling position, and a sample analyzer configured to create an analysis result corresponding to the specimen, wherein it is configured to create report data including the diagnostic image and the analysis result as image data and create sample data including the sampling position and the analysis result as document data. Note that the term "data" refers to information handled by a computer. Further note that the image data denotes data (data group) including color information and position information composed of a plurality of data of a bit unit and not including a character code. Further note that the document data denotes data (data group) of character codes composed of a plurality of data of a bit unit.

As described above, the diagnostic imaging system according to one aspect of the present invention is configured to create report data as image data and create sample data as document data. With this, a doctor, etc., can not only view the diagnostic image and the analysis result included in the report data as images, but also use the sampling position and the analysis result included in the sample data as character codes (document data). As a result, it becomes unnecessary to re-input the analysis result as an image displayed as image data as document data. For this reason, when a doctor, etc., creates a document from the information included in the report data, it is possible to reduce the labor for creating the document.

In the diagnostic imaging system according to the one aspect of the present invention, it is preferable to further include a data creation information processing device configured to create the report data as image data by using the diagnostic image and the analysis result and create the sample data by using the analysis result as the sampling position and the document data. With this configuration, since the report data and the sample data are not created by the radiographic imaging device and the sample analyzer, a system for creating report data and sample data can be built by using an existing radiographic imaging device and an existing sample analyzer as it is.

In this case, preferably, in the data creation information processing device, it is configured such that the diagnostic image and the analysis result be input to the report data and the analysis result be input to the sample data based on the information on the subject. With such a configuration, the diagnostic image and the analysis result corresponding to the information on the subject are automatically input to the report data and the analysis result corresponding to the information on the subject is automatically inputted to the sample data. Therefore, it is possible to reduce the labor for inputting by the creator of the report data and the sample data.

In the diagnostic imaging system equipped with the data creation information processing device, it is preferable that the diagnostic imaging system further include: a first server configured to store the report data; a second server configured to store the sample data; and a diagnostic information processing device capable of acquiring the report data of the first server and the sample data of the second server. With this configuration, in the diagnostic information processing device, not only the report data stored this time but also the previous report data stored in the first server can be acquired, and it is also possible to acquire not only the sample data stored this time but also the previous sample data stored in the second server.

In this case, it is preferable that the radiographic imaging device, the sample analyzer, the data creation information processing device, the first server, the second server, and the diagnostic information processing device be respectively connected via a network. With this configuration, it is possible to easily transmit and receive commands and data among the radiographic imaging device, the sample analyzer, the data creation information processing device, the first server, the second server, and the diagnostic information processing device.

In the diagnostic imaging system equipped with the diagnostic information processing device, it is preferable that the analysis result included in the sample data be acquired so as to be utilized as numeric data as document data in the diagnostic information processing device. With this configuration, when the analysis result is numeric data, it becomes easier to perform numerical calculation and other processing on the analysis result, so a doctor, etc., can easily create a document by utilizing the analysis result included in the sample data. Note that the numeric data denotes data (data group) of character codes corresponding to numbers composed of a plurality of data of a bit unit.

In the diagnostic imaging system according to the one aspect of the present invention, it is preferable that in the sample data, the sampling position be specified by a blood vessel name. With this configuration, it is possible to easily grasp the sampling position in the diagnostic image.

In the diagnostic imaging system according to the one aspect of the present invention, it is preferable that the report data be created as image data in tabular form which further includes the sampling position together with the analysis result. With this configuration, it becomes possible to easily find the sampling position in the diagnostic image of the specimen corresponding to the analysis result.

In this case, it is preferable that in the report data, the sampling position and the analysis result in tabular form having the same appearance and the same content as each of the sampling position and the analysis result in the sample data as document data be displayed as image data. With this configuration, it is possible to create report data by using the sample data in tabular form as it is, so it is possible to reduce the labor for creating report data.

DESCRIPTION OF PREFERRED EMBODIMENTS

Hereinafter, embodiments of the present invention will be described with reference to the drawings.

With reference to FIG. 1 to FIG. 6, the configuration of the diagnostic imaging system 1 according to the present embodiment will be described. The diagnostic imaging system 1 is configured to perform a local diagnosis by sampling a specimen of a subject T. Specifically, in the diagnostic imaging system 1, X-ray imaging for sampling a specimen and an analysis of the sampled specimen are performed.

Diagnostic Imaging System

Examples of a local diagnosis using the diagnostic imaging system 1 include adrenal vein sampling for diagnosis of primary aldosteronism, a selective arterial calcium injection test for diagnosis of insulinoma, and endoscopic biopsy performed by sampling an internal organs tissue piece using an endoscope.

Figure 1:
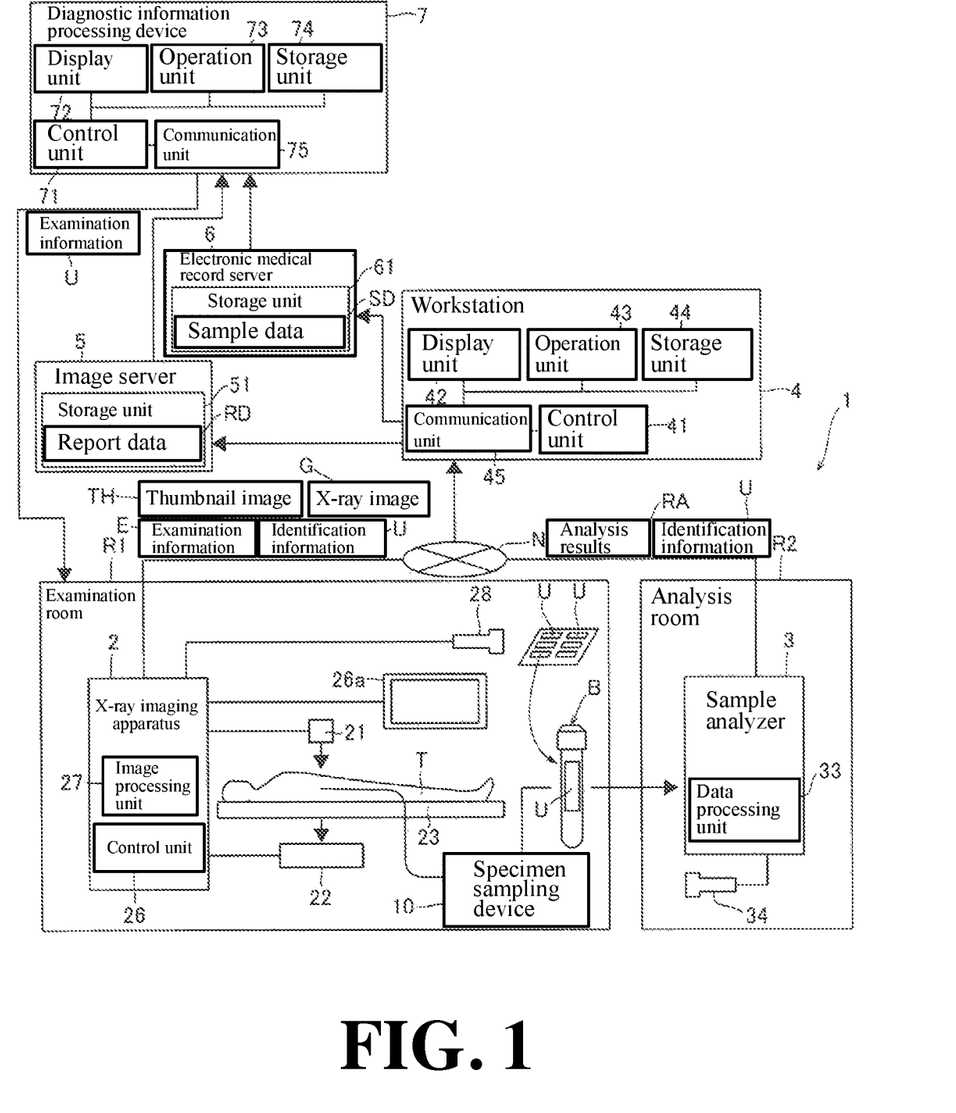
FIG. 1 is a block diagram showing an entire configuration of a diagnostic imaging system according to an embodiment of the present invention.

As shown in FIG. 1, the diagnostic imaging system 1 is provided with an X-ray imaging apparatus 2 for capturing an X-ray image G of a subject T and a sample analyzer 3 for analyzing specimens sampled from the subject T. Here, the X-ray imaging apparatus 2 and the sample analyzer 3 are separately installed in an examination room R1 and an analysis room R2, respectively. Note that the X-ray imaging apparatus 2 is an example of the "radiographic imaging device" recited in claims.

Further, the diagnostic imaging system 1 is provided with a workstation 4, an image server 5, an electronic medical record server 6, and a diagnostic information processing device 7. The workstation 4 is configured to create report data RD and sample data SD based on the analysis result RA of the X-ray image G and the specimen. The image server 5 is configured to store the report data RD. The electronic medical record server 6 is configured to store the sample data SD. The diagnostic information processing device 7 is configured so that the report data RD obtained from the image server 5 and the sample data SD obtained from the electronic medical record server 6 can be browsed. Note that the workstation 4, the image server 5, and the electronic medical record server 6 are examples of the "data creation information processing device", the "first server", and the "second server" recited in claims, respectively.

The diagnostic imaging system 1 captures an image of organs G from the outside of the subject T by the X-ray imaging apparatus 2 for the purpose of sampling a specimen in the subject T. When sampling a specimen, a specimen sampling device 10 is introduced into an inside of a subject T, and a doctor in charge of sampling a specimen advances the specimen sampling device 10 to the sampling position of the specimen by using the captured image of the X-ray image G as a clue to sample the specimen.

For adrenal vein sampling, a catheter is used as the specimen sampling device 10.

The sampled specimen is taken into the specimen sampling device 10 and separately accommodated in a specimen container B for accommodating a specimen, and thereafter the specimen container B is transferred to the sample analyzer 3. In the sample analyzer 3, when an operator such as a doctor sets the specimen container B in the sample analyzer 3, the sample analyzer 3 accepts the specimen. The specimen container B is, for example, a blood collection tube. The sample analyzer 3 analyzes the acquired specimen.

Here, to the specimen container B, specimen identification information for specifying the specimen is assigned. The specimen identification information is identification information U attached to the specimen container B for accommodating the sampled specimen. The identification information U is, for example, a specimen ID attached to the specimen container B in the form of a barcode or a two-dimensional code. The identification information U is prepared, for example, in the form of a label printed with a barcode, and is attached to the specimen container B by an operator when a specimen is sampled.

X-Ray Imaging Apparatus

Figure 2:
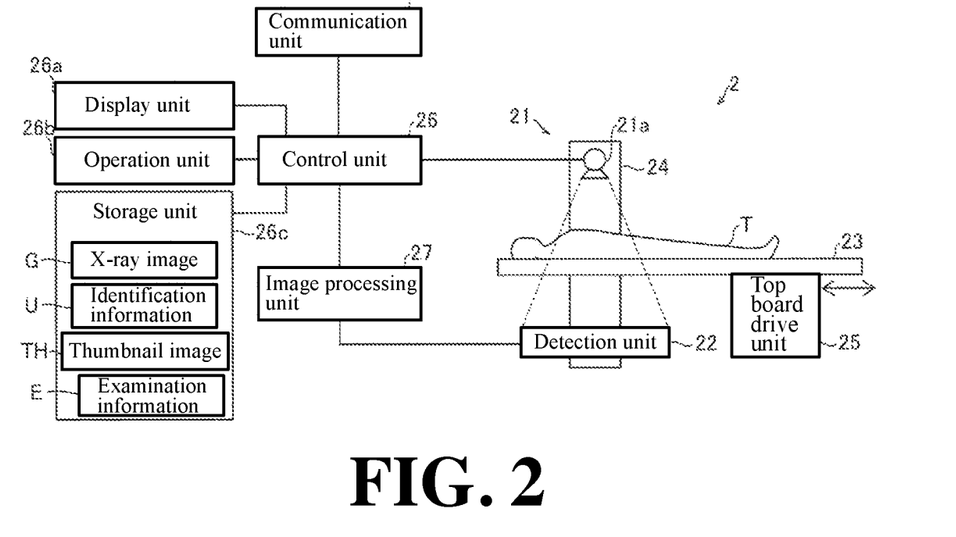
FIG. 2 is a block diagram illustrating a configuration example of an X-ray imaging apparatus of a diagnostic imaging system according to an embodiment of the present invention.

As shown in FIG. 2, the X-ray imaging apparatus 2 is an apparatus for capturing an image of an X-ray image G for imaging an inside of a subject T by irradiating radiation from the outside of the subject T.

The X-ray imaging apparatus 2 is provided with an irradiation unit 21 for irradiating radiation (X-rays) to the subject T and a detection unit 22 for detecting the radiation transmitted through the subject T. The irradiation unit 21 and the detection unit 22 are arranged so as to face each other across the top board 23 on which a subject T is placed. The irradiation unit 21 and the detection unit 22 are movably supported by the moving mechanism 24. The top board 23 is movable in the horizontal direction by the top board drive unit 25. The irradiation unit 21, the detection unit 22, and the top board 23 are moved via the moving mechanism 24 and the top board drive unit 25 so that the area-of-interest of the subject T can be imaged. The area-of-interest is an area including the sampling position of the specimen in the subject T. The X-ray imaging apparatus 2 is provided with a control unit 26 for controlling the moving mechanism 24 and the top board drive unit 25.

The irradiation unit 21 includes a radiation source 21*a*. The radiation source 21*a* is, for example, an X-ray tube that generates X-rays by applying a predetermined high voltage. The irradiation unit 21 is connected to the control unit 26. The control unit 26 controls the irradiation unit 21 according to preset imaging conditions and generates X-rays from the radiation source 21*a*.

The detection unit 22 detects X-rays irradiated from the irradiation unit 21 and transmitted through the subject T, and outputs a detection signal corresponding to the detected X-ray intensity. The detection unit 22 is formed of, for example, an FPD (Flat Panel Detector). The X-ray imaging apparatus 2 is provided with an image processing unit 27 configured to acquire an X-ray detection signal from the detection unit 22 and generate an X-ray image G based on the detection signal of the detection unit 22. The detection unit 22 outputs a detection signal of a predetermined resolution to the image processing unit 27.

The image processing unit 27 is a computer composed of, for example, a processor such as a CPU (Central Processing Unit) (not shown) and storage units (not shown) such as a ROM (Read Only Memory) (not shown) and a RAM (Random Access Memory) (not shown), and functions as an image processing unit 27 by having the processor execute an image processing program. In addition to generate an X-ray image G, the image processing unit 27 has a function of performing correction processing for improving the visibility of the X-ray image G and synthesis processing for synthesizing a plurality of X-ray images G. In addition, the image processing unit 27 performs processing for generating a thumbnail image TH (see FIG. 5) of the generated X-ray image G.

The control unit 26 is a computer including a CPU (not shown), a ROM (not shown), a RAM (not shown), and the like. The control unit 26 functions as a control unit 26 that controls each part of the X-ray imaging apparatus 2 by executing a predetermined control program by the CPU. The control unit 26 controls the irradiation unit 21 and the image processing unit 27, and controls the driving of the moving mechanism 24 and the top board drive unit 25.

The X-ray imaging apparatus 2 is provided with a display unit 26*a*, an operation unit 26*b*, and a storage unit 26*c*. Further, the X-ray imaging apparatus 2 is provided with a communication unit 26*d* for connecting with the network N. The display unit 26*a* is, for example, a monitor such as, e.g., a liquid crystal display. The operation unit 26*b* is configured to include, for example, a keyboard, a mouse, a touch panel, another controller, or the like. The storage unit 26*c* is configured by a storage device, such as, e.g., a hard disk drive. The control unit 26 is configured to perform control to display the image generated by the image processing unit 27 on the display unit 26*a*. Further, the control unit 26 is configured to accept an input operation via the operation unit 26*b*. The storage unit 26*c* is configured to store data of an X-ray image G, data of identification information U, data of a thumbnail image TH, examination information E, and the like. The examination information E is an example of the "information on the subject" recited in claims.

As shown in FIG. 1, the X-ray imaging apparatus 2 is provided with a reading unit 28 for reading the identification information U attached to the specimen container B for accommodating a sampled specimen. The reading unit 28 is, for example, a bar code reader (two-dimensional code reader) corresponding to the identification information U, and is capable of reading the identification information U attached to the specimen container B.

The control unit 26 is configured to assign the identification information U read by the reading unit 28 to the X-ray image G when the specimen is sampled. Further, the control unit 26 is configured to assign examination information E, which is data on a patient, when the X-ray image G is captured.

Sample Analyzer

Figure 3:
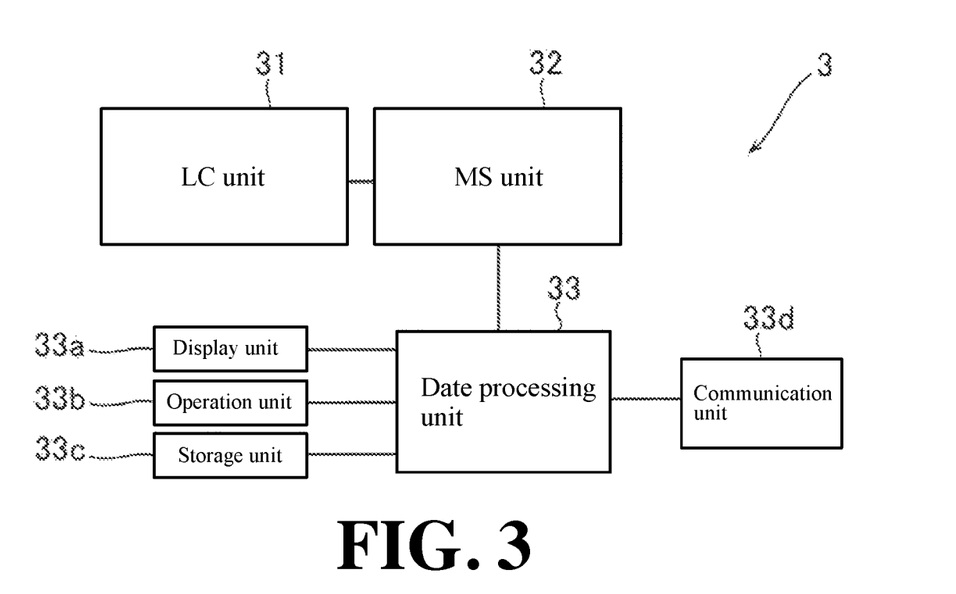
FIG. 3 is a block diagram showing a configuration example of a sample analyzer of a diagnostic imaging system according to an embodiment of the present invention.

The sample analyzer 3 is a device that acquires a specimen sampled from a subject T, performs measurement of components necessary for diagnosis, and detects a cell, etc. The sample analyzer 3 is, for example, a blood analysis device for analyzing blood components, a blood cell classification device, and a chemical analysis device. The object to be measured or detected by the sample analyzer 3 varies depending on the type of disease to be diagnosed, so it is selected according to the type of disease.

As an example of the sample analyzer 3, FIG. 3 shows a sample analyzer 3 composed of a liquid chromatograph mass spectrometer. The sample analyzer 3 is provided with a liquid chromatograph unit 31 (hereinafter referred to as an LC unit 31) which separates the target components contained in the specimen and a mass spectrometer 32 (hereinafter referred to as an MS unit 32) which ionizes the separated target components and separates and detects the target ions according to the mass number.

The LC unit 31 mainly includes a carrier liquid reservoir (not shown) for accommodating a carrier liquid, a liquid delivery pump (not shown) for delivering the carrier liquid together with the specimen, a sample introduction unit (not shown) for introducing the specimen, and a separation column (not shown) for separating the specimen in the carrier liquid for each component.

The MS unit 32 is provided at the subsequent stage of the LC unit 31, and mainly includes an ionization unit (not shown) for ionizing the sample components separated by the LC unit 31, a mass separator (not shown) for mass separating the generated ions and passing through specific ions, and an ion detector (not shown) for detecting ions which passed through the mass separator. The MS unit 32 outputs a detection signal for each mass with respect to the sample components eluted sequentially from the LC unit 31.

The sample analyzer 3 is provided with a data processing unit 33 that performs component analysis based on the detection signal of the MS unit 32. The data processing unit 33 conducts a quantitative analysis of predetermined components (cortisol, aldosterone, etc.) in a specimen by preparing a mass spectrum from the detection signal for each mass and comparing it with a known calibration curve.

As shown in FIG. 3, the sample analyzer 3 is provided with a display unit 33a, an operation unit 33b, a storage unit 33c, and a communication unit 33d. The sample analyzer 3 is further provided with a reading unit 34. The data processing unit 33 is configured to assign the identification information U read by the reading unit 34 to the analysis result RA when the specimen is analyzed. With this, the analysis result RA and the X-ray image G are associated with each other via a common identification information U.

Workstation

Here, a report data RD is created to convey information that can be read from the X-ray image G to the doctor, etc., by using the analysis result RA of the sampled specimen and the X-ray image G capable of specifying the sampling position of the sampled specimen. However, since the report data RD is created as image data, it is possible to extract the analysis result RA of the specimen as an image, but it is difficult to extract the analysis result RA of the specimen as numeric data. Note that the image data denotes data (data group) including color information and position information composed of a plurality of data on a bit basis and not including a character code. Further note that the numeric data denotes data (data group) of character codes corresponding to numbers composed of a plurality of data of a bit unit.

For this reason, when a doctor, etc., creates a document from the information included in the report data RD, it takes time and effort to prepare the document.

Under the circumstances, in the diagnostic information processing device 7 of this embodiment, it is configured such that not only the report data RD as image data but also the sample data SD as document data are created by a user in the workstation 4. Note that the document data denotes data (data group) of character codes composed of a plurality of data of a bit unit. Hereinafter, the workstation 4 will be described with reference to FIG. 1, FIG. 4, and FIG. 5.

Specifically, the workstation 4 is provided with a control unit 41, a display unit 42, an operation unit 43, and a storage unit 44. Further, the workstation 4 is provided with a communication unit 45 for connecting with the network N.

The control unit 41 is configured to cause the display unit 42 to display the X-ray image G and the thumbnail image TH acquired from the X-ray imaging apparatus 2. Further, the control unit 41 is configured to cause the display unit 42 to display the analysis result RA obtained from the sample analyzer 3. Further, the control unit 41 is configured to accept an input operation via the operation unit 43. The storage unit 44 is configured to store data of the examination information E, data of the X-ray image G, data of the thumbnail image TH, data of the identification information U, and data of the analysis result RA of the specimen. The communication unit 45 is communicably connected to the X-ray imaging apparatus 2, the sample analyzer 3, the image server 5, and the electronic medical record server 6 via the network N.

The control unit 41 is configured to acquire a plurality of X-ray images G from the X-ray imaging apparatus 2. Specifically, based on the fact that data of a plurality of X-ray images G is transmitted from the X-ray imaging apparatus 2, the control unit 41 acquires the data of a plurality of X-ray images G via the network N by the communication unit 45. Here, to each of data of the plurality of X-ray images G, corresponding examination information E and identification information U are assigned. Therefore, the control unit 41 obtains data of the plurality of X-ray images G and also obtains corresponding examination information E and identification information U.

The control unit 41 is configured to acquire a plurality of analysis results RA from the sample analyzer 3. Specifically, based on the fact that data of a plurality of analysis results RA is transmitted from the sample analyzer 3, the control unit 41 acquires data of the plurality of analysis results RA via the network N by the communication unit 45. Here, since the corresponding identification information U is assigned to each of the plurality of analysis result RA, the control unit 41 acquires data of the plurality of analysis results RA and acquires the corresponding identification information U.

The control unit 41 is configured to acquire a plurality of thumbnail images TH (see FIG. 5) corresponding to each of the plurality of X-ray images G from the X-ray imaging apparatus 2. Specifically, based on the fact that data of a plurality of thumbnail images TH has been transmitted from the X-ray imaging apparatus 2, the control unit 41 acquires data of the plurality of thumbnail images TH via the network N by the communication unit 45. Since the corresponding examination information E and identification information U are assigned to each of data of the plurality of thumbnail images TH, the control unit 41 acquires a plurality of thumbnail images TH data and also acquires the corresponding examination information E and identification information U.

Then workstation 4 is configured to create sample data SD based on the data of the examination information E, the data of the identification information U and the data of the analysis result RA of the specimen. Here, the analysis result RA is numeric data. Further, the workstation 4 is configured to create the report data RD based on the data of the examination information E, the data of the X-ray image G, the data of the thumbnail image TH, the data of the identification information U, and the data of the analysis result RA of the specimen. Hereinafter, the sample data SD and the report data RD will be described in detail.

Sample Data

Figure 4:
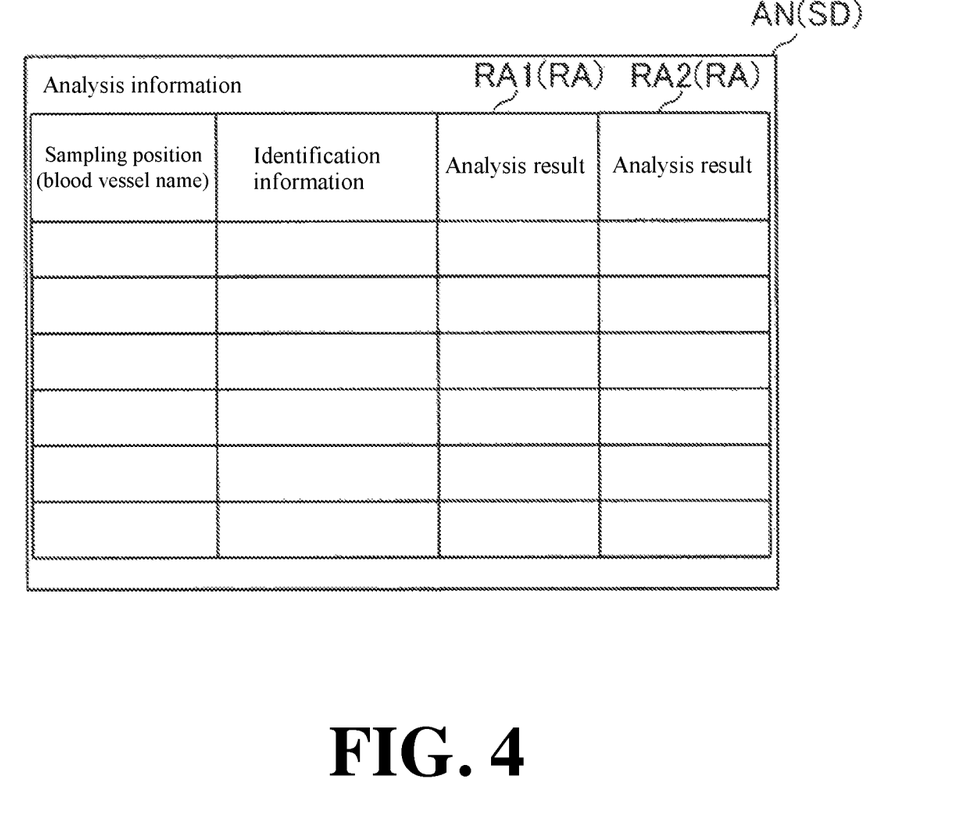
FIG. 4 is a schematic diagram showing a display screen of sample data in the diagnostic imaging system according to an embodiment of the present invention.

As shown in FIG. 4, the sample data SD is created as document data including the sampling position and the analysis result RA having an analysis result RA1 and an analysis result RA2. Note that the analysis result RA1 and the analysis result RA2 are numeric data indicating component amounts of different components (e.g., aldosterone and cortisol).

Specifically, the sample data SD includes analysis information AN. The analysis information AN includes a plurality of specific information including the sampling position of each of the plurality of specimens. The analysis information AN includes a plurality of items of "Sampling Position (blood vessel name)", "Identification Information U", "Analysis Result RA1" and "Analysis Result RA2". In the analysis information AN, the user registers information, such as, e.g., the sampling position (blood vessel name), the identification information U, the analysis result RA1, and the analysis result RA2 in the arbitrary specimen among the plurality of specimens in corresponding items. Hereinafter, a plurality of several items of analysis information AN in an arbitrary specimen of a plurality of specimens will be described.

"Sampling Position" is an item in which the name of the blood vessel corresponding to the position where specimen is sampled is registered. "Identification Information U" is an item in which the identification information U attached to the specimen container B in which specimen is stored is registered. "Analysis Result RA1" is an item in which one of a plurality of analysis results RA obtained by analyzing the specimen in the sample analyzer 3 is registered as numeric data. "Analysis Result RA2" is an item in which the other of a plurality of analysis results RA obtained by analyzing the specimen in the sample analyzer 3 is registered as numeric data. Here, the information on the identification information U and the analysis results RA1 and RA2 are automatically registered in the corresponding item based on the fact that the workstation 4 acquired the analysis results RA1 and RA2 to which the identification information U is attached from the sample analyzer 3. Further, the information on the sampling position (blood vessel name) is manually registered in the corresponding item by the user in the workstation 4.

Further, when the analysis information AN is displayed on the display unit 42, a plurality of items, such as, e.g., Sampling Position, Identification Information U, Analysis Result RA1, and Analysis Result RA2 are listed for each of a plurality of specimens. Note that the list display is an example of the "tabular form" recited in claims.

Report Data

Figure 5:
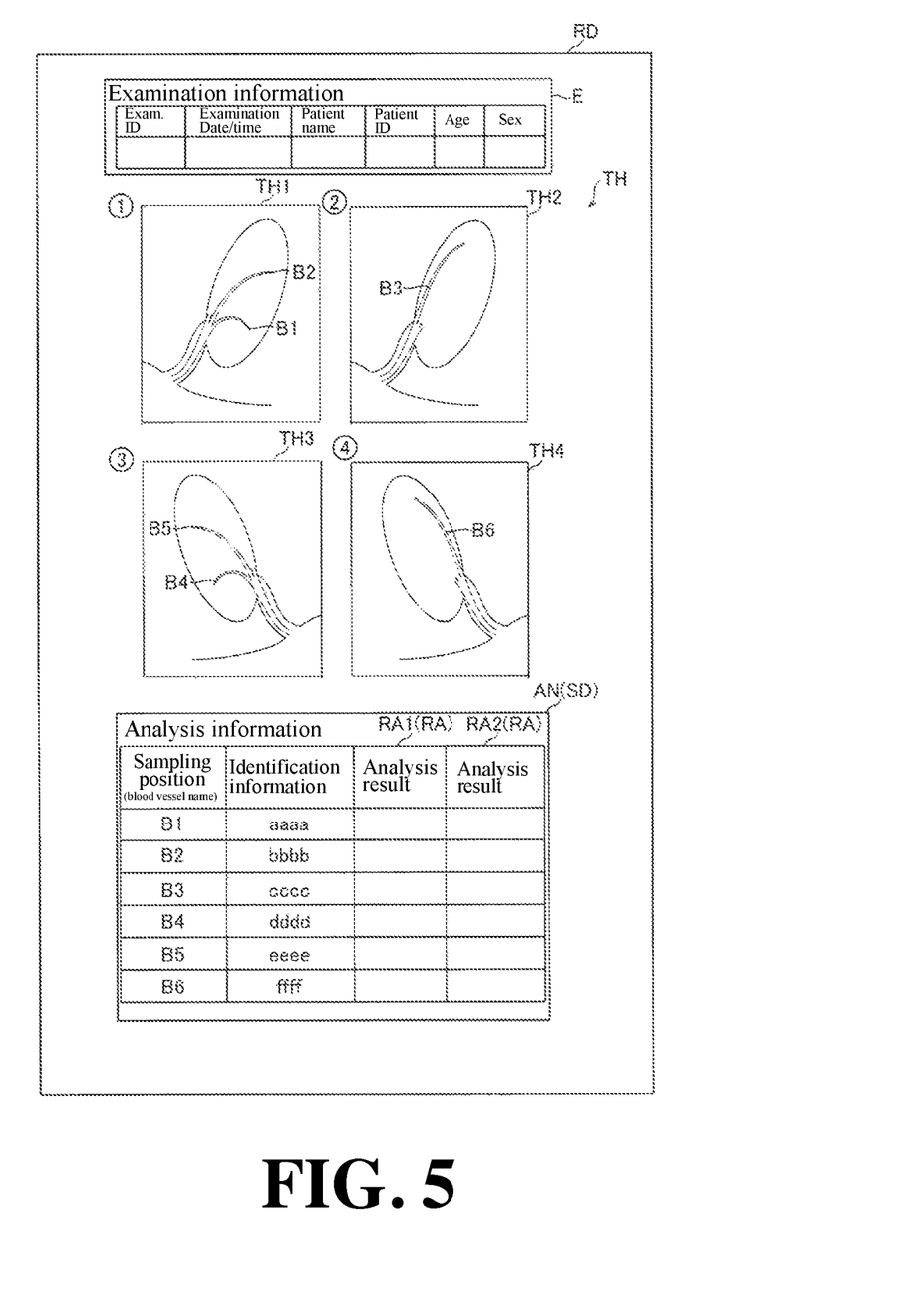
FIG. 5 is a schematic diagram showing a display screen of report data in the diagnostic imaging system according to an embodiment of the present invention.

As shown in FIG. 5, the report data RD is created as image data including the X-ray image G and the analysis results RA1 and RA2. Specifically, the report data RD includes the examination information E, the X-ray image G, and the analysis information AN. On the display screen of the report data RD, the examination information E, the X-ray image G, and the analysis information AN are arranged in this order from the top. In the analysis information AN, the analysis information AN described in the sample data SD is displayed as the same format and image data of the same contents.

That is, the analysis information AN has the same format and contents as the analysis information AN described in the sample data SD, and has a plurality of specific information including the sampling positions of each of the plurality of specimens. The analysis information AN includes a plurality of items of Sampling Position (blood vessel name), Identification Information U, Analysis Result RA1, and Analysis Result RA2. Here, the analysis information AN is automatically registered by acquiring the analysis results RA1 and RA2 including the corresponding identification information U by the workstation 4 based on the fact that the workstation 4 acquired the X-ray image G to which the identification information U was assigned from the X-ray imaging apparatus 2. Then, in the state in which the list is displayed, the analysis information AN is included as a part of the report data RD which is image data.

The examination information E has a plurality of items, such as, e.g., "Examination ID", "Examination Date and Time", "Patient Name", "Patient ID", "Age", and "Sex". "Examination ID" is an item in which the ID unique to the performed examination is registered. "Examination Date and Time" is an item in which the date and time when the examination was performed is registered. "Patient Name" is an item in which the name of the patient who received the examination is registered. "Patient ID" is an item in which an ID corresponding to a patient name is registered. "Age" and "Sex" are items for which age and sex of a patient are registered, respectively. Here, the information on the examination ID, the examination date and time, the patient name, the patient ID, and the age are automatically registered in the corresponding item based on the fact that the workstation 4 acquired the X-ray image G to which the examination information E is assigned from the X-ray imaging apparatus 2. Then, in the state in which the list is displayed, the examination information E is included as a part of the report data RD which is image data.

In the display screen of the report data RD, the X-ray image G is displayed as a thumbnail image TH. The thumbnail image TH is a plurality of thumbnail images TH corresponding to the plurality of X-ray images G captured by the X-ray imaging apparatus 2, respectively. The plurality of thumbnail images TH includes a first thumbnail image TH1, a second thumbnail image TH2, a third thumbnail image TH3, and a fourth thumbnail image TH4 in order from the upper left end. Here, the first thumbnail image TH1, the second thumbnail image TH2, the third thumbnail image TH3, and the fourth thumbnail image TH4 are images obtained by reducing the X-ray image G. Here, the first through fourth thumbnail images TH4 are automatically registered based on the fact that the workstation 4 acquired the X-ray image G to which the examination information E was assigned from the X-ray imaging apparatus 2. In a state in which the first to fourth thumbnail images TH1 to TH4 are arranged as described above, the first to fourth thumbnail images TH1 to TH4 are included as it is as a part of the report data RD which is image data.

In each of the plurality of thumbnail images TH, blood vessels that can specify each of a plurality (six) of sampling positions are displayed. Here, the blood vessels displayed in the first thumbnail image TH1 are denoted as a first blood vessel B1 and a second blood vessel B2 in order from the bottom. The blood vessel displayed in the second thumbnail image TH2 is denoted as a third blood vessel B3. Further, the blood vessels displayed in the third thumbnail image TH3 are denoted as a fourth blood vessel B4 and a fifth blood vessel B5 in order from the bottom. The blood vessel displayed in the fourth thumbnail image TH4 is denoted as a sixth blood vessel B6.

In the first thumbnail image TH1, the sampling position of the specimen sampled from the first blood vessel B1 and the sampling position of the specimen sampled from the second blood vessel B2 can be specified. In the second thumbnail image TH2, the sampling position of the specimen sampled from the third blood vessel B3 can be specified. In the third thumbnail image TH3, the sampling position of the specimen sampled from the fourth blood vessel B4 and the sampling position of the specimen sampled from the fifth blood vessel B5 can be specified. In the fourth thumbnail image TH4, the sampling position of the specimen sampled from the sixth blood vessel B6 can be specified.

Image Server

As shown in FIG. 1, the image server 5 is configured to store the report data RD (see FIG. 5) created in the workstation 4 and provides the acquired report data RD to the diagnostic information processing device 7. Specifically, the image server 5 is provided with a control unit (not shown), a display unit (not shown), an operation unit (not shown), and a storage unit 51. The image server 5 is also provided with a communication unit (not shown) for connecting with the network N. Based on the instruction from the workstation 4, the control unit obtains and saves the report data RD from the workstation 4 via the network N by the communication unit. Further, the control unit provides the report data RD stored in the storage unit 51 to the diagnostic information processing device 7 via the network N by the communication unit based on the instruction from the diagnostic information processing device 7.

As described above, the image server 5 functions as a so-called PACS (Picture Archiving and Communication Systems). The report data RD including the thumbnail image TH of the X-ray image G is stored in the image server 5 in a format conforming to a DICOM (Digital Imaging and Communication in Medicine).

Electronic Medical Record Server

As shown in FIG. 1, the electronic medical record server 6 is configured to store data of a clinical record for each patient. Further, the electronic medical record server 6 is configured to store the sample data SD (see FIG. 4) generated in workstation 4 and provides the sample data SD stored in the diagnostic information processing device 7. Specifically, the electronic medical record server 6 is provided with a control unit (not shown), a display unit (not shown), an operation unit (not shown), and a storage unit 61. Further, the electronic medical record server 6 is provided with a communication unit (not shown) for connecting with the network N.

Based on the instruction from the workstation 4, the control unit obtains and stores the sample data SD from the workstation 4 via the network N by the communication unit. Further, the control unit provides the sample data SD stored in the storage unit 61 to the diagnostic information processing device 7 via the network N by the communication unit based on the instruction from the diagnostic information processing device 7. As described above, the sample data SD provided to the diagnostic information processing device 7 is used by a doctor, etc., to create various materials. The various materials include, for example, statistical materials made into tables such as histograms after extracting numeric data of the analysis results RA1 and RA2.

Diagnostic Information Processing Device

As shown in FIG. 1, the diagnostic information processing device 7 is provided with a control unit 71, a display unit 72, an operation unit 73, and a storage unit 74. The diagnostic information processing device 7 is further provided with a communication unit 75 for connecting with the network N.

The control unit 71 is configured to acquire the sample data SD (see FIG. 4) created in the workstation 4 from the electronic medical record server 6. Further, the control unit 71 is configured to cause the display unit 72 to display the sample data SD obtained from the electronic medical record server 6. The control unit 71 is configured to acquire the report data RD (see FIG. 5) created in the workstation 4 from the image server 5. Further, the control unit 71 is configured to cause the display unit 72 to display the report data RD acquired from the image server 5.

The control unit 71 is configured to accept an input operation via the operation unit 73. The storage unit 74 is configured to store the sample data SD, the report data RD, and the like. The communication unit 75 is communicably connected to each of the electronic medical record server 6 and the image server 5 via the network N.

Flowchart of Preparation Process of Sample Data and Report Data

Figure 6:
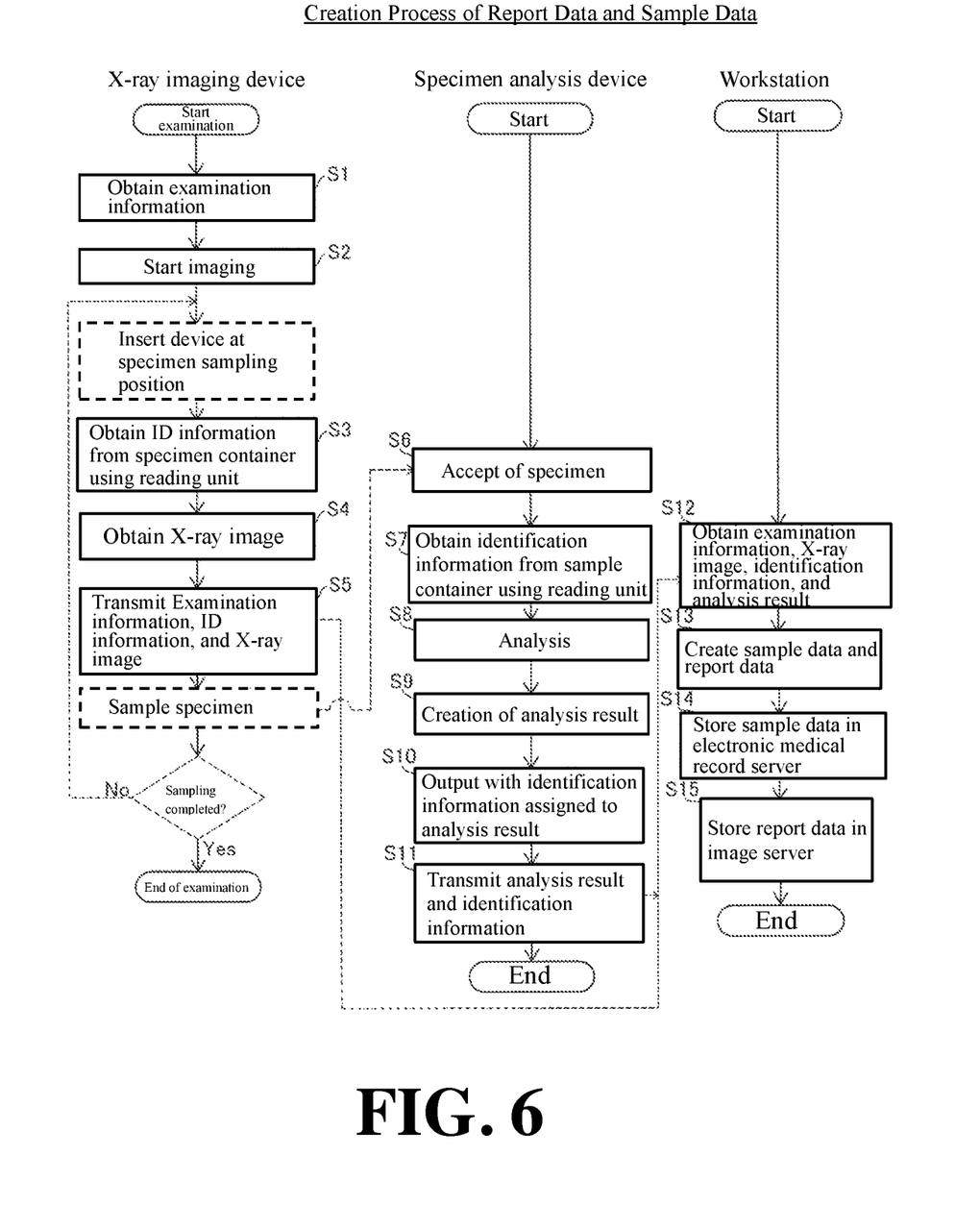
FIG. 6 is a flowchart of a process flow for creating sample data and report data in the diagnostic imaging system according to an embodiment of the present invention.

With reference to FIG. 6, a process flow of creating the sample data SD and the report data RD by the X-ray imaging apparatus 2, the sample analyzer 3, and the workstation 4 will be described.

In Step S1, the X-ray imaging apparatus 2 acquires examination information E, which is information on the patient, from the diagnostic information processing device 7, based on a request from a doctor, etc., to the patient. In Step S2, the X-ray imaging apparatus 2 starts imaging the X-ray image G and displays the fluoroscopic image of the subject T in the moving image format on the display unit 26a. When the specimen sampling device 10 is placed at a sampling position, in Step S3, the control unit 26 acquires the identification information U from the specimen container B using the reading unit 28. That is, the operator selects an arbitrary label on which the identification information U has been printed using the reading unit 28 and reads the identification information U. The label from which the identification information U has been read is affixed to the specimen container B for accommodating the present specimen by the operator.

In Step S4, the control unit 26 acquires an X-ray image G (still image) when the specimen is sampled. At this time, the control unit 26 adds the examination information E acquired in Step S1 to the X-ray image G and records it. Further, the control unit 26 adds the identification information U acquired in Step S3 to the X-ray image G and records it. In Step S5, the control unit 26 transmits the examination information E, the identification information U, and the X-ray image G to the workstation 4.

The specimen is accommodated within the specimen container B. The specimen container B accommodating the specimen is transported to the analysis room R2 where the sample analyzer 3 is installed by the operator.

Steps S2 to S5 are repeated until all the specimens required for this adrenal vein sampling are sampled.

On the other hand, the sample analyzer 3 accepts the specimen in Step S6. That is, the specimen container B accommodating the specimen is set in the sample analyzer 3. In Step S7, the data processing unit 33 acquires the identification information U from the specimen container B using the reading unit 34. That is, the operator reads the identification information U attached to the specimen container B using the reading unit 34.

In Step S8, the sample analyzer 3 analyzes the accepted specimen. In Step S9, the data processing unit 33 creates analysis results RA1 and RA2. In Step S10, the data processing unit 33 adds the identification information U to the analysis results RA1 and RA2 of the specimen and outputs it. Then, in Step S11, the data processing unit 33 transmits the analysis results RA1 and RA2 and the identification information U to the workstation 4.

In Step S12, the workstation 4 acquires the examination information E, the X-ray image G, the identification information U, and the analysis results RA1 and RA2. That is, the workstation 4 acquires the X-ray image G to which the examination information E and the identification information U have been assigned from the X-ray imaging apparatus 2. Then, the workstation 4 acquires the analysis results RA1 and RA2 to which the identification information U has been assigned from the sample analyzer 3.

In Step S13, the workstation 4 creates report data RD and sample data SD based on the examination information E, the X-ray image G, the identification information U, and the analysis results RA1 and RA2. Here, the sample data SD is created as document data including the identification information U and the analysis results RA1 and RA2. The report data RD is created as image data including the examination information E, the X-ray image G, the identification information U, and the analysis results RA1 and RA2.

That is, in the workstation 4, the identification information U and the analysis results RA1 and RA2 of the sample data SD are automatically registered based on the examination information E. Then, in the workstation 4, the sampling position (blood vessel name) of the sample data SD is manually registered by the user. With this, the sample data SD is created.

In the workstation 4, the analysis results RA1 and RA2 corresponding to the examination information E, the thumbnail image TH, and the identification information U are automatically registered based on the examination information E. With this, the report data RD is created.

In Step S14, the control unit 41 stores the sample data SD in which all the necessary items of the examination information E and the analysis information AN have been entered in the electronic medical record server 6. As a result, the sample data SD is stored in the electronic medical record server 6 as document data so that it can be provided to the diagnostic information processing device 7.

In Step S15, the control unit 41 stores the report data RD in which all necessary items of the examination information E, the thumbnail image TH, and the analysis information AN have been input in the image server 5. With this, the report data RD is stored as image data in the image server 5 so that it can be provided to the diagnostic information processing device 7.

Effects of this Embodiment

In this embodiment, the following effects can be obtained.

In this embodiment, as described above, the diagnostic imaging system 1 is provided with the X-ray imaging apparatus 2 and the sample analyzer 3. Further, the diagnostic imaging system 1 is configured to create not only the report data RD which is image data including the X-ray image G and the analysis results RA1 and RA2 but also the sample data SD which is document data including the sampling position and the analysis results RA1 and RA2. With this, a doctor, etc., can use not only the diagnostic image and the analysis results RA1 and RA2 included in the report data RD as an image but also the sampling position and the analysis results RA1 and RA2 included in the sample data SD as character codes. As a result, it becomes unnecessary to re-input the analysis results RA1 and RA2 as an image displayed as image data as document data. For this reason, when a doctor, etc., creates a document from the information included in the report data RD, it is possible to reduce the labor for creating the document.

In this embodiment, as described above, the diagnostic imaging system 1 is provided with the workstation 4 which creates the report data RD as image data using the X-ray image G and the analysis results RA1 and RA2 and creates the sample data SD as document data by using the sampling position and the analysis results RA1 and RA2. As a result, since the report data RD and the sample data SD are not created by the X-ray imaging apparatus 2 and the sample analyzer 3, it is possible to build a system for creating the report data RD and the sample data SD by using the existing X-ray imaging apparatus 2 and sample analyzer 3 as it is.

Further, in this embodiment, as described above, in the workstation 4, the X-ray image G and the analysis results RA1 and RA2 are input to the report data RD based on the examination information E, and the analysis results RA1 and RA2 are input to the sample data SD. As a result, the X-ray image G corresponding to the examination information E and the analysis results RA1 and RA2 are automatically input to the report data RD and the analysis results RA1 and RA2 corresponding to the examination information E are automatically input to the sample data SD. Therefore, it is possible to reduce the labor for inputting by the creator of the report data RD and the sample data SD.

Further, in this embodiment, as described above, the diagnostic imaging system 1 is provided with the image server 5 in which the report data RD is stored and the electronic medical record server 6 in which the sample data SD is stored. In addition, the diagnostic imaging system 1 is further provided with the diagnostic information processing device 7 capable of acquiring each of the report data RD of the image server 5 and the sample data SD of the electronic medical record server 6. Thus, in the diagnostic information processing device 7, it is possible to acquire not only the report data RD stored this time but also the previous report data RD stored in the image server 5. It is also possible to acquire not only the sample data SD stored this time but also the previous sample data SD stored in the electronic medical record server 6.

In this embodiment, as described above, the X-ray imaging apparatus 2, the sample analyzer 3, the workstation 4, the image server 5, the electronic medical record server 6, and the diagnostic information processing device 7 are connected via the network N, respectively. This makes it possible to easily transmit and receive commands and data among the X-ray imaging apparatus 2, the sample analyzer 3, the workstation 4, the image server 5, the electronic medical record server 6, and the diagnostic information processing device 7.

Further, in this embodiment, as described above, in the sample data SD, the sampling position is specified by the blood vessel name. As a result, it is possible to easily grasp the sampling position in the X-ray image G.

Further, in this embodiment, as described above, the analysis results RA1 and RA2 included in the sample data SD can be obtained so as to be utilized as numeric data as document data in the diagnostic information processing device 7. As a result, in cases where the analysis results RA1 and RA2 are numeric data, it becomes easier to perform numerical calculations and other processing on the analysis results RA1 and RA2, so a doctor, etc., can easily create material by using the analysis results RA1 and RA2 included in the sample data SD.

Further, in this embodiment, as described above, the report data RD is created as image data which further includes sampling positions along with analysis results RA1 and RA2. This makes it easier to find the sampling positions in the first to fourth thumbnail images TH1 to TH4 of the specimens corresponding to the analysis results RA1 and RA2.

Further, in this embodiment, as described above, in the report data RD, the sampling position in the sample data SD as document data, the sampling position and the analysis results having the same appearance and the same contents as each of the sampling positions in the sample data SD as document data and the analysis results RA1 and RA2 are displayed in tabular form as image data. This makes it possible to create the report data RD by using the sample data SD as it is, thus reducing the labor for creating the report data RD.

Modified Embodiment

It should be understood that the embodiments disclosed here are examples in all respects and are not restrictive. The scope of the present invention is shown by the claims rather than the descriptions of the embodiments described above, and includes all changes (modifications) within the meaning of equivalent and the scope of claims.

For example, in the above-described embodiment, the example in which the X-ray image G is displayed as the thumbnail image TH on the display screen of the report data RD is shown, but the present invention is not limited thereto. For example, on the display screen of the report data, the X-ray image may be displayed as it is.

In the above-described embodiment, the diagnostic imaging system 1 is provided with the electronic medical record server 6 and the image server 5, but the present invention is not limited thereto. In the present invention, a server integrating the electronic medical record server and the image server may be provided.

In the above-described embodiment, an example in which the sample data SD and the report data RD are created in the workstation 4 is described, but the present invention is not limited to this. In the present invention, the sample data and the report data may be created in the X-ray imaging apparatus or the sample analyzer.

Further, in the above-described embodiment, an example in which the specimen is blood is described, but the present invention is not limited thereto. In the present invention, the specimen may be a tissue piece or the like.

Further, in the above-described embodiment, an example is described in which the examination information E and the analysis information AN of the report data RD are the same as the examination information E and the analysis information AN of the sample data SD, respectively, but the present invention is not limited thereto. In the present invention, each of the examination information and the analysis information of the report data may be different from the examination information and the analysis information of the sample data.

Further, in the above-described embodiment, an example in which the examination information E, the thumbnail image TH of the X-ray image G, and the analysis information AN are shown in the report data RD is described, but the present invention is not limited to this. In the present invention, for example, a finding by a doctor may be additionally shown in the report data.

Further, in the above-described embodiment, the example in which the examination information E is arranged above the analysis information AN on the display screen of the sample data SD is described, but the present invention is not limited thereto. For example, the examination information and the analysis information may be arranged side by side, and the placement position is not particularly limited.

Further, in the above-described embodiment, the example in which the examination information E, the X-ray image G, and the analysis information AN are arranged in order from the top on the display screen of the report data RD is described, but the present invention is not limited thereto. For example, the examination information, the X-ray image, and the analysis information may be arranged side by side, and the placement position is not particularly limited.

Further, in the above-described embodiment, for convenience of explanation, the example in which the control processing of the X-ray imaging apparatus 2, the sample analyzer 3, and the workstation 4 is described using a flowchart of a flow driving type in which the processing is sequentially performed according to the processing flow is described, but the present invention is not limited to this. In the present invention, the control processing of the X-ray imaging apparatus, the sample analyzer, and the workstation may be performed by event-driven type processing that executes processing on an event-by-event basis. In this case, it may be performed in a completely event driven manner, or may be performed by a combination of event driving and flow driving.

Further, in the above-described embodiment, the example in which sample data includes numeric data is described, but the present invention is not limited to this. In the present invention, the sample data may be character data, and may not include numeric data.

The invention claimed is:
1. A diagnostic imaging system comprising:
a radiographic imaging device configured to capture a diagnostic image of a subject;
a sample analyzer configured to analyze a specimen extracted from the subject and create an analysis result of the specimen as document data; and
a workstation comprising a communication unit and a control unit,
wherein the communication unit is configured to acquire the analysis result and the diagnostic image,
wherein the control unit is configured to accept a registration of the sampling position of the specimen, which is analyzed by the sample analyzer to create the analysis result, and create sample data including the analysis result and the sampling position of the specimen as document data,
wherein the control unit is configured to convert the sample data including the analysis result and the sampling position to image data and combine the converted sample data with the acquired diagnostic image to create report data as image data, and wherein the communication unit is configured to transmit the report data as image data to a first server and transmit the sample data as document data to a second server.

2. The diagnostic imaging system as recited in claim 1, further comprising:
   the first server configured to store the report data;
   the second server configured to store the sample data; and
   a diagnostic information processing device configured to receive the report data of the first server and the sample data of the second server.

3. The diagnostic imaging system as recited in claim 2, wherein the radiographic imaging device, the sample analyzer, the workstation, the first server, the second server, and the diagnostic information processing device are respectively connected via a network.

4. The diagnostic imaging system as recited in claim 2, wherein the analysis result included in the sample data is acquired so as to be utilized as numeric data of document data in the diagnostic information processing device.

5. The diagnostic imaging system as recited in claim 2, wherein the workstation is configured to display a first image corresponding to the received report data, the first image including the diagnostic image and the analysis result.

6. The diagnostic imaging system as recited in claim 5, wherein the workstation is configured to display a second image including the analysis result using the received sample data.

7. The diagnostic imaging system as recited in claim 6, wherein the report data does not include a character code, and
   wherein the sample data comprises character codes.

8. The diagnostic imaging system as recited in claim 6, wherein the first image and the second image include the analysis result displayed in the same format.

9. The diagnostic imaging system of claim 2, wherein the first server is configured to store the report data in a format conforming to DICOM (Digital Imaging and Communication in Medicine).

10. The diagnostic imaging system as recited in claim 1, wherein in the sample data, the corresponding sampling position is specified by a blood vessel name.

11. The diagnostic imaging system as recited in claim 1, wherein the report data is created as image data which includes the corresponding sampling position together with the analysis result in tabular form.

12. The diagnostic imaging system as recited in claim 11, wherein in the report data, the corresponding sampling position and the analysis result in tabular form have the same appearance and the same content as each of the corresponding sampling position and the analysis result in the sample data when displayed.

13. The diagnostic imaging system as recited in claim 1, wherein the sample analyzer is configured to analyze a specimen of the subject that has been extracted from the subject.

14. The diagnostic imaging system of claim 1, wherein the sample analyzer comprises a blood analysis device.

15. The diagnostic imaging system of claim 1, wherein the sample analyzer comprises a liquid chromatograph mass spectrometer.

16. The diagnostic imaging system of claim 1, wherein the radiographic imaging device is configured to transmit the diagnostic image together with identification information to the workstation and the sample analyzer is configured to separately transmit the analysis result together with identification information to the workstation.

17. The diagnostic imaging system of claim 16, wherein at least one of the radiographic imaging device and the sample analyzer comprises a bar code reader configured to read the identification information.

18. The diagnostic imaging system of claim 16, wherein both the report data and the sample data comprise the identification information.

* * * * *